US00PP35405P2

(12) United States Plant Patent
Carter

(10) Patent No.: US PP35,405 P2
(45) Date of Patent: Sep. 26, 2023

(54) *SALVIA* PLANT NAMED 'JAMMIN JAZZ'

(50) Latin Name: ***Salvia* x *guaranitica***
Varietal Denomination: Jammin Jazz

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 18/082,240

(22) Filed: Dec. 15, 2022

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

(56) References Cited

PUBLICATIONS https://www.tapatalk.com/groups/featheredfriends/salvia-bodacious-jammin-jazzberry-t40114.html; Dec. 31, 2021; 9 pages.*
https://online.flippingbook.com/view/522050/; 2022; 8 pages.*
https://twitter.com/FBTScom; Nov. 29, 2022; 2 pages.*
https://mailchi.mp/fbts/ordering-for-2023-starts-today-1095346; Feb. 7, 2023; pages.*
chrome-extension://efaidnbmnnnibpcajpcglclefindmkaj/https://www.zyromski.com/media/wysiwyg/SFZ_BDC_-_2022-2023_Quality_Cuttings-KD.pdf; Feb. 7, 2023; pages.*
https://planthaven.com/plant/salvia-bodacious-jammin-jazz/; Feb. 8, 2023; 3 pages.*

* cited by examiner

*Primary Examiner* — Kent L Bell
(74) *Attorney, Agent, or Firm* — Weatherly IP Solutions, LLC; James M. Weatherly

(57) ABSTRACT

A new cultivar of *Salvia* x *guaranitica* named 'Jammin Jazz' that is distinguishable by its compact well-branched plant habit and its early production of bright saturated red flowers from March until October.

2 Drawing Sheets

Genus and species: *Salvia* x *guaranitica*.
Variety denomination: 'Jammin Jazz'.

BACKGROUND

The present disclosure relates to a new and distinct cultivar of *Salvia* plant, also known as a sage, a perennial that is grown for use as an ornamental landscape and container plant. The new variety is known botanically as *Salvia* x *guaranitica* and will be referred to hereinafter by the cultivar name 'Jammin Jazz'.

'Jammin Jazz' originated and was selected from a population of hybrid seedlings from a *Salvia* breeding program, which was started in 2010. The breeding program was conducted in the inventor's greenhouse nursery in Elk, Calif. The aim of the breeding program is to develop a uniform series of compact free-flowering varieties of *Salvia* x *guaranitica* each with similar plant habits and flowering characteristics but with distinctly different or unusual flower colors. 'Jammin Jazz' was selected by the inventor in 2020 from seedlings which resulted from the controlled hybridization of the inventor's variety 'Cool Wild Watermelon' (unpatented) by the inventor's variety "RF 2020-004" (unreleased, unpatented). Seed from the female parent was grown out, and one seedling, the instant variety, was selected for its unusual red flower color for the *guaranitica* species. The red flower color is further accentuated by its very dark calyx.

'Jammin Jazz' was first asexually propagated in 2020 in a greenhouse at the inventor's nursery in Elk, Calif. using softwood tip and stem cuttings. The inventor has confirmed that 'Jammin Jazz' is stable and reproduces true to type in successive generations of asexual reproduction.

SUMMARY

The following traits have been repeatedly observed and represent the distinguishing characteristics of 'Jammin Jazz'. 'Jammin Jazz' has not been tested under all possible conditions and phenotypic differences may be observed with variations in environmental, climatic, and cultural conditions, without however, any variance in genotype.

1. 'Jammin Jazz' exhibits a compact well-branched plant habit.
2. 'Jammin Jazz' bears bright saturated red flowers from March until October.
3. 'Jammin Jazz' grows and flowers rapidly. Flowering plants may be produced in 10 to 12 weeks from a cutting.

DESCRIPTION OF THE PHOTOGRAPHS

The accompanying color photographs illustrate the overall appearance of the new *Salvia* cultivar 'Jammin Jazz' showing the colors as true as it is reasonably possible to obtain in colored reproductions of this type. Photographs were taken in December 2022 in Santa Barbara, Calif. from a one-year-old plant grown in the open ground outdoors, with one pinch after initial cutting establishment and without any chemical growth regulators. Colors in the photographs may differ from the color values cited in the detailed botanical description, which accurately describe the observed colors of the new variety 'Jammin Jazz'.

DESCRIPTION OF THE NEW VARIETY

Figure 1:
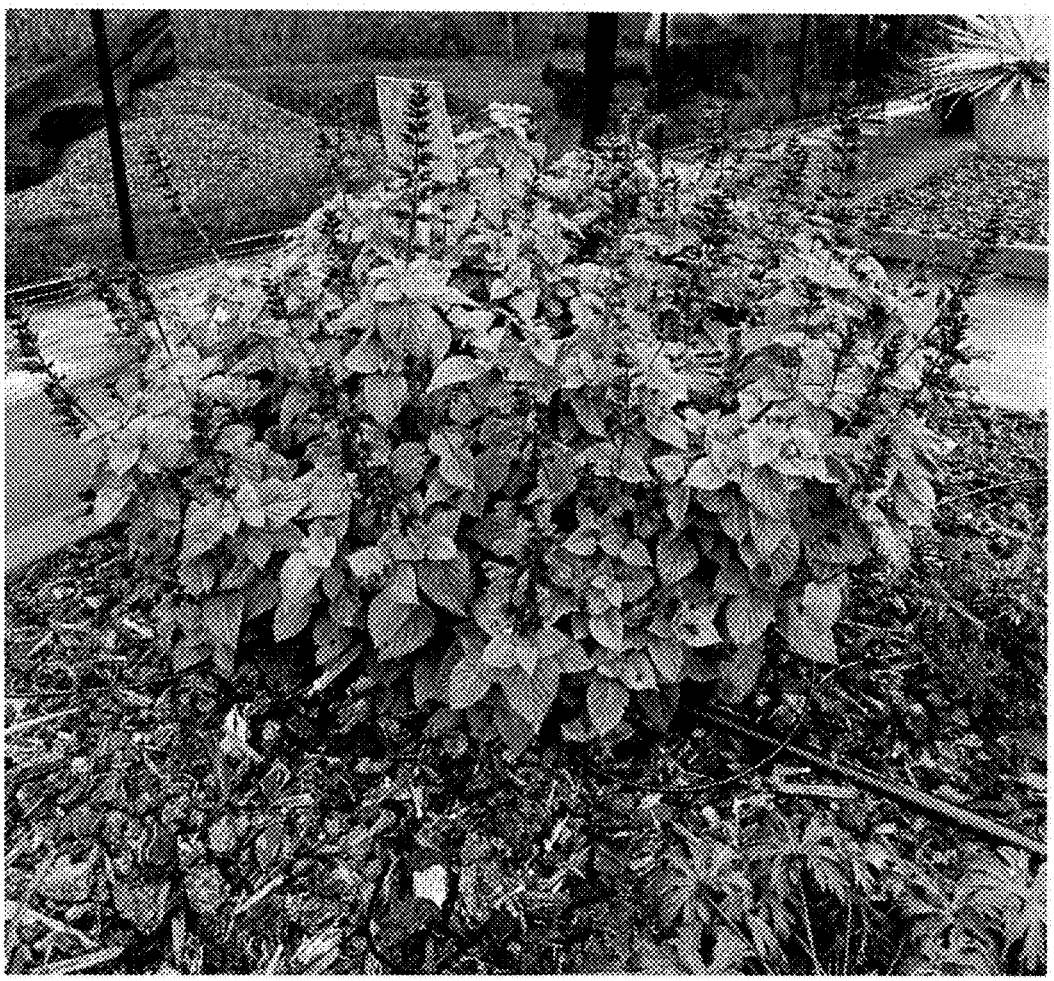
FIG. 1 depicts an entire plant of 'Jammin Jazz'.
Figure 2:
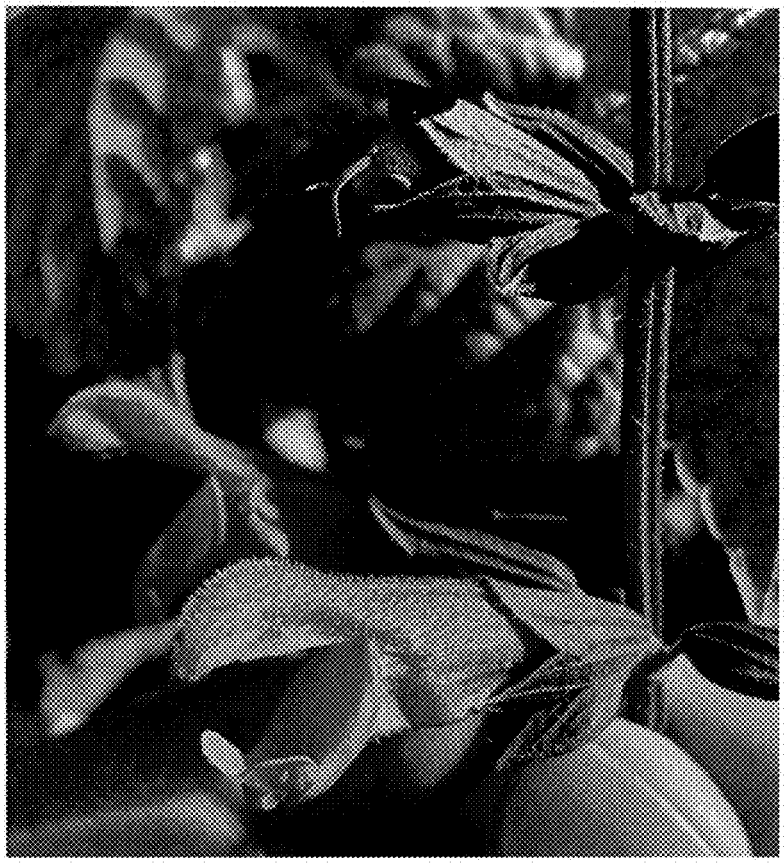
FIG. 2 depicts a close-up view of the inflorescences of 'Jammin Jazz'.

The following detailed descriptions set forth the distinctive characteristics of 'Jammin Jazz'. Observations, measurements, values, and comparisons were collected in July 2022 in Santa Barbara, Calif. from a six-months-old plant which had been growing outdoors in full sun in a 2-gallon container in Santa Barbara, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—x *guaranitica*.

*Common name*.—Sage.

Parentage:

*Female parent*.—'Cool Wild Watermelon' (unpatented).

*Male parent*.—*Salvia* code number "RF 2020-004" (unreleased inventor's variety).

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 12 weeks are required to produce a budded and flowering plant in a quart container. Larger containers require a longer period of growth in order to fill out. Flowering will continue throughout spring, summer and fall.

*Suggested container size*.—Quart to two-gallon container.

*Use*.—Ornamental for use as a landscape plant or container plant.

*Type*.—Perennial.

*Overall dimensions*.—After one year's growth in a 2-gallon container, 80 cm in height including the inflorescence, and 50 cm in width.

*Cultural requirements*.—Grow in full sun with moderate water and well-draining soil.

*Hardiness*.—USDA Zone 8.

*Form*.—Upright vase-shaped.

*Growth habit*.—Compact.

*Blooming season*.—From one month after breaking spring dormancy to first frost.

*Lastingness of blooms*.—Inflorescence has some flower for 14 days, individual flowers last for 2 to 3 days.

Stems (below first pinch):

*Condition*.—Lignified.

*Bark*.—Papery, splitting.

*Shape*.—Round.

*Length*.—1.0 cm to 1.5 cm.

*Diameter*.—6.0 mm.

*Bark color*.—Ranges between N199C and N200A.

*Stem color* (*where exposed beneath bark*).—144C.

*Shape*.—Terete.

*Texture*.—Rough.

Branches:

*Quantity*.—12-15 primary basal branches, each bearing 3-5 pairs of secondary branches at each node. All branches bear a terminal inflorescence.

*Shape*.—Square section with protruding rounded rib-like corners.

*Length*.—35 cm to 40 cm measured to base of inflorescence.

*Width*.—7 mm at base, 3 mm at base of inflorescence.

*Internode length*.—7 cm-10 cm (primary branches); 2.5 cm-4 cm (secondary branches).

*Color*.—144A to 144B with longitudinal streaks of anthocyanin pigmentation 187C becoming darker 187A towards and within the inflorescence.

Leaves:

*Type, arrangement*.—Simple, opposite.

*Attachment*.—Petiolate.

*Quantity per branch*.—5-6 pairs below inflorescence.

*Shape*.—Cordate.

*Length* (*mature*).—7 cm, occasional solitary large leaf 9.5 cm.

*Width* (*mature*).—Up to 5.5 cm, occasional solitary large leaf 9.0 cm.

*Margin*.—Dentate, 18-20 teeth on each leaf side, teeth facing towards apex, depth 1.5 mm.

*Thickness*.—Moderately thick, slightly stiff.

*Surface* (*adaxial*).—Slightly raised between veins, smooth, glabrous, semi-glossy.

*Surface* (*abaxial*).—Smooth, glabrous, matte.

*Color* (*adaxial surface*).—143C.

*Color* (*abaxial surface*).—143D.

*Venation*.—Pinnate, adaxial surface veins slightly depressed, abaxial veins prominently raised.

*Vein color*.—As leaf surfaces, except abaxial midrib exhibits anthocyanin pigmentation 187C towards the petiole.

*Apex*.—Acute.

*Base*.—Cuneate.

*Fragrance*.—None.

*Stipules*.—Present as very small terminal leaves in each axil, sessile or very short petiolate, maximum observed dimensions 18 mm in length, 12 mm in width, surfaces and colors as leaves, margins finely dentate.

Petiole:

*Shape*.—Sulcate, concave surface uppermost.

*Length*.—3 cm.

*Width*.—3 mm at stem attachment, 2 mm at leaf base.

*Texture*.—Puberulent.

*Color*.—Juvenile growth 146D soon becoming saturated with anthocyanin pigmentation, color 187C.

Peduncle:

*Length* (*from uppermost leaf pair to base of lowest whorl of flowers*).—Increases as inflorescence develops, initially 2 cm, finally 8 cm.

*Shape*.—Square.

*Width*.—2.5 mm to 3 mm.

*Texture*.—Puberulent.

*Color*.—184B.

Inflorescence:
*Type*.—Terminal raceme.
*Flower arrangement*.—In 10 to 12 discrete whorls each with 8 flowers mostly, occasionally in whorls of 6 or 10 flowers.
*Length*.—20 cm when fully developed (uppermost whorl of flowers open).
*Width*.—8 cm.

Pedicel:
*Length*.—4 mm.
*Diameter*.—1 mm.
*Texture*.—Puberulent.
*Color*.—184B.

Calyx:
*Shape*.—Campanulate, sepal lobes fused then flared toward the apex.
*Length*.—15 mm.
*Width at base*.—3 mm.
*Width across sepal apices*.—11 mm.

Sepals:
*Quantity*.—2, longitudinally fused towards base, free flared apical lobes.
*Sepal length*.—15 mm.
*Sepal width*.—8 mm when flattened.
*Shape*.—Boat shaped.
*Apex* (*upper sepal*).—Acute.
*Apex* (*lower sepal*).—Rounded except for small notch at apex, depth of notch 1.5 mm.
*Base*.—Truncate.
*Margin*.—Entire.
*Texture*.—Adaxial surface: Smooth, matte, longitudinally ribbed. Ribs 1 mm apart, raised less than 0.1 mm. Abaxial surface: Glabrous, glossy.
*Color* (*both surfaces*).—Between 187A and N79A.

Flowers:
*Quantity*.—Typically 8 flowers in each whorl, occasionally 6 or 10 flowers per whorl; 10-12 whorls per inflorescence.
*Aspect*.—Flowers horizontal, outward-facing, encircling three-quarters of stem circumference.
*Shape*.—Tubular, two-lipped.
*Blooming period*.—From March until October.
*Persistence*.—Self-cleaning.
*Fragrance*.—Slight pleasant sage fragrance.

Bud:
*Shape*.—Ellipsoidal on emergence from calyx.
*Dimensions* (*immediately before petal emergence*).—12 mm in length, 5 mm in diameter.
*Color*.—53B.
*Surface*.—Strongly pubescent, hairs dense, fine, up to 0.5 mm in length, hair color 62C.

Corolla:
*Shape*.—Tubular proximally to two-lipped distally, lower lip attitude relative to corolla is downward.
*Length*.—25 mm including corolla tube length 5 mm.
*Width*.—9 mm in vertical plane, 5 mm in horizontal plane.
*Texture*.—Glossy.
*Color* (*both surfaces*).—61B, except tube base NN155D, translucent.

Petals:
*Quantity*.—2.
*Arrangement*.—One upper petal and one lower petal which appears as a large prominent lip with two lateral lobes fused to the lip and to each other.
*Upper petal*.—Shape: Hooded. Length: 12 mm. Width: 5 mm. Texture: Adaxial surface: Strongly pubescent. Hairs dense, fine, 1 mm in length, hair color 61B. Abaxial surface: Glabrous. Apex: Rounded, with cluster of fine hairs approximately 1 mm in length, hair color 62C. Base: Truncate. Margin: Smooth, entire. Color (both surface): 52A.
*Lower petal, lip*.—Shape: Broad cordate with apical notch. Length: 9 mm from petal base to base of apical notch. Width: 5 mm-6 mm. Texture (both surfaces): Smooth, glabrous. Apex: Emarginate, depth of notch 1 mm. Base: Truncate. Margin: Entire, gently undulating. Color (both surfaces): 52A.
*Lower petal, lateral lobes*.—Shape: Elliptic, fused at base, the pair appear as wings. Length (each lateral lobe): 8 mm. Width: 4 mm. Texture: Adaxial surface: Lightly puberulent. Abaxial surface: Smooth, glabrous, matte. Apex: Rounded. Base: Truncate. Margin: Smooth, entire except for very short fine hairs at the base, hair color 52A. Color (both surfaces): 52A.

Reproductive organs:
*Stamens*.—Quantity: 2. Filaments: 15 mm in length, of which 7 mm basally fused, 8 mm free. Filament color: N66B at base becoming N66C towards anthers.
*Anthers*.—Attachment, shape: Basally attached, longitudinally boat shaped. Width: 0.75 mm. Color: 187A (adaxial surface), 163B (abaxial, inner surface).
*Pollen*.—Amount: Sparse. Color: 15D.
*Pistil*.—Quantity: 1. Style: 33 mm in length to base of short forked stigma, diameter 0.5 mm, color 83D. Stigma: Bifid, each fork slightly recurved, 1.5 mm-2.0 mm in length, diameter 0.5 mm, color 83A.
*Ovary* (*only observed unfertilized*).—Shape: Short vertical cylindrical, rounded apex, comprises 4-5 undeveloped capsules. Dimensions: 2.5 mm in height, 2.0 mm in diameter. Color: 151D.

Seed:
*Quantity*.—Sparse.
*Shape*.—Ovoid.
*Dimensions*.—2 mm in length, 1.5 mm in diameter.
*Surface*.—Pitted, mottled.
*Color*.—200B.

Disease and pest susceptibility: Susceptible to aphids (*aphis gossypii*) when stressed. Generally outgrows most bacterial and viral infections. Resistant to deer and rabbit grazing.

Drought tolerance: Drought tolerant.

COMPARISON WITH PARENTAL LINES AND KNOWN VARIETY

In comparison with the inventor's male parent variety, code number "RF 2020-004", the flowers of 'Jammin Jazz' are red in color whereas the flowers of "RF 2020-004" are deep maroon in color and are also larger than the flowers of 'Jammin Jazz.

In comparison with the inventor's female parent variety, 'Cool Wild Watermelon', the flowers of 'Jammin Jazz' are red in color whereas the flowers of 'Cool Wild Watermelon' are pale pink in color. In addition, 'Cool Wild Watermelon' is a much larger variety and is also more vigorous than 'Jammin Jazz'.

'Jammin Jazz' is closest overall to *Salvia* 'Big Pink' (unpatented) which is also a variety of *Salvia* x *guaranitica*. Whereas 'Jammin Jazz' bears red flowers, the flowers of 'Big Pink' are pink in color, and the growth habit of 'Big Pink' is much larger and more vigorous than the compact plant habit of 'Jammin Jazz'.

I claim:

1. A new and distinct cultivar of *Salvia* Plant Named 'Jammin Jazz' as described and illustrated herein.

* * * * *